US010100091B2

(12) United States Patent
Chen

(10) Patent No.: US 10,100,091 B2
(45) Date of Patent: Oct. 16, 2018

(54) FUSION PROTEIN FOR HIV-1 GP120 ANTIGEN DETECTION

(71) Applicant: Arizona Board of Regents, for and on behalf of, Arizona State University, Scottsdale, AZ (US)

(72) Inventor: Shengxi Chen, Chandler, AZ (US)

(73) Assignee: ARIZONA BOARD OF REGENTS, for and on behalf of, ARIZONA STATE UNIVERSITY, Scottsdale, AZ (US)

(*) Notice: Subject to any disclaimer, the term of this patent is extended or adjusted under 35 U.S.C. 154(b) by 86 days.

(21) Appl. No.: 15/029,152

(22) PCT Filed: Oct. 14, 2014

(86) PCT No.: PCT/US2014/060457
§ 371 (c)(1),
(2) Date: Apr. 13, 2016

(87) PCT Pub. No.: WO2015/057688
PCT Pub. Date: Apr. 23, 2015

(65) Prior Publication Data
US 2016/0237122 A1 Aug. 18, 2016

Related U.S. Application Data

(60) Provisional application No. 61/890,491, filed on Oct. 14, 2013.

(51) Int. Cl.
*C07K 14/00* (2006.01)
*G01N 33/569* (2006.01)

(52) U.S. Cl.
CPC ............ *C07K 14/001* (2013.01); *C07K 14/00* (2013.01); *G01N 33/56983* (2013.01); *C07K 2319/21* (2013.01); *G01N 2333/162* (2013.01); *G01N 2800/26* (2013.01); *G01N 2800/52* (2013.01)

(58) Field of Classification Search
CPC ........................... C07K 14/00; C07K 2319/21
See application file for complete search history.

(56) References Cited

U.S. PATENT DOCUMENTS

| | | | |
|---|---|---|---|
| 6,303,299 B1 | 10/2001 | Hecht et al. | |
| 2003/0187247 A1 | 10/2003 | Burton et al. | |
| 2011/0263485 A1* | 10/2011 | LiWang | A61K 9/08 514/3.8 |

FOREIGN PATENT DOCUMENTS

WO    WO 2015/057688    4/2015

OTHER PUBLICATIONS

Iwakura, M., et al., 1992, Dihydrofolate reductase as a new "affinity handle", J. Biochem. 111:37-45.*
Mellors, J.W. et al., "Prognosis in HIV-1 Infection Predicted by the Quantity of Virus in Plasma", In Science, vol. 272, No. 5265, May 1996, pp. 1167-1170.
Gilbert, M. et al., "Enzyme-Linked Immunoassay for Human Immunodeficiency Virus Type 1 Envelope Glycoprotein 120", In the Journal of Clinical Microbiology, vol. 29, No. 1, Jan. 1991, pp. 142-147.
Rychert, J. et al., "Detection of HIV gp120 in Plasma during Early HIV Infection is Associated with Increased Proinflammatory and Immunoregulatory Cytokines", In AIDS Research and Human Retroviruses, vol. 26, No. 10, Oct. 2010, pp. 1139-1145.
Wyatt, R. et al., "The Antigenic Structure of the HIV gp120 Envelope Glycoprotein", In Nature, vol. 393, No. 6686, Jun. 1998, pp. 705-711.
Wyatt, R. and Sodroski, J., "The HIV-1 Envelope Glycoproteins: Fusogens, Antigens, and Immunogens", In Science, vol. 280, No. 5371, Jun. 1998, pp. 1884-1888.
Kwong, P.D. et al., "Structure of an HIV gp120 Envelope Glycoprotein in Complex with the CD4 Receptor and a Neutralizing Human Antibody", In Nature, vol. 393, Jun. 1998, pp. 648-659.
Moebius, U. et al., "The Human Immunodeficiency Virus gp120 Binding Site on CD4: Delineation by Quantitative Equilibrium and Kinetic Binding Studies of Mutants in Conjunction with a High-Resolution CD4 Atomic Structure", In the Journal of Experimental Medicine, vol. 176, No. 2, Aug. 1992, pp. 507-517.
Huang, C.C. et al., "Scorpion—Toxin Mimics of CD4 in Complex with Human Immunodeficiency Virus gp120: Crystal Structures, Molecular Mimicry, and Neutralization Breadth", In Structure, vol. 13, No. 5, May 2005, pp. 755-768.
Duca, M. et al., "Aminoacylation of Transfer RNAs with One and Two Amino Acids", In Methods, vol. 44, No. 2, Feb. 2008, pp. 87-99.
Chen, S. and Hecht, S.M., "Synthesis of pdCpAs and Transfer RNAs Activated with Derivatives of Aspartic Acid and Cysteine", In Bioorganic and Medicinal Chemistry, vol. 16, No. 19, Oct. 2008, pp. 9023-9031.
Chen, S. et al., "Synthesis of pdCpAs and Transfer RNAs Activated with Thiothreonine and Derivatives", In Bioorganic and Medicinal Chemistry, vol. 20, No. 8, Apr. 2012, pp. 2679-2689.
Chen, S. et al., "Two Pyrenylalanines in Dihydrofolate Reductase Form an Excimer Enabling the Study of Protein Dynamics", In the Journal of the American Chemical Society, vol. 134, No. 46, Nov. 2012, pp. 18883-18885.
Nangreave, R.C. et al., "A New Strategy for the Synthesis of Bisaminoacylated tRNAs", In Organic Letters, vol. 13, No. 18, Sep. 2011, pp. 4906-4909.
Maini, R. et al., "Incorporation of β-amino acids into Dihydrofolate Reductase by Ribosomes having Modifications in the Peptidyltransferase Center", In Bioorganic and Medicinal Chemistry, vol. 21, No. 5, Mar. 2013, pp. 1088-1096.
Sulimenko, T. and Draber, P., "A Fast and Simple Dot-Immunobinding Assay for Quantification of Mouse Immunoglobulins in Hybridoma Culture Supernatants", In the Journal of Immunological Methods, vol. 289, No. 1-2, Jun. 2004, pp. 89-95.
Lee, K.-H. et al., "Ribosomal Synthesis and in Situ Isolation of Peptide Molecules in a Cell-Free Translation System", In Protein Expression and Purification, vol. 71, No. 1, May 2010, pp. 16-20.

(Continued)

*Primary Examiner* — Jeffrey S Parkin
(74) *Attorney, Agent, or Firm* — Byrne Poh LLP; Nina R. Horan

(57) ABSTRACT

The present disclosure relates to novel fusion proteins that bind to the HIV-1 gp120 antigen. The present disclosure also relates to nucleic acids, plasmids and host cells that comprise a sequence that encodes the fusion proteins of the disclosure. The fusion proteins of the disclosure can be used in applications to detect the presence of HIV-1 gp120 protein, to detect an HIV-1 infection and to monitor treatment of an HIV-1 infection.

3 Claims, 6 Drawing Sheets

Specification includes a Sequence Listing.

(56) References Cited

OTHER PUBLICATIONS

Loose, C.R. et al., "Optimization of Protein Fusion Partner Length for Maximizing in Vitro Translation of Peptides", In Biotechnology Progress, vol. 23, No. 2, Mar./Apr. 2007, pp. 444-451.
Santosuosso, M. et al., "HIV-1 Envelope Protein gp120 is Present at High Concentration in Secondary Lymphoid Drgans of Individuals with Chronic HIV-1 Infection", In the Journal of Infectious Diseases, vol. 200, No. 7, Oct. 2009, pp. 1050-1053.
Klasse, P.J. and Moore, J.P., "Is There Enough gp120 in the Body Fluids of HIV-1-Infected Individuals to Have Biologically Significant Effects?", In Virology, vol. 323, No. 1, May 2004, pp. 1-8.
Oh, S.K. et al., "Identification of HIV-1 Envelope Glycoprotein in the Serum of AIDS and ARC Patients", In the Journal of Acquired Immune Deficiency Syndromes, vol. 5, No. 3, Mar. 1992, pp. 251-256.
Abcam, "Dihydrofolate Reductase (DHFR) Protein (Active) ab87755", Product Datasheet, last accessed Apr. 26, 2016, pp. 1-3, available at: http://www.abcam.com/recombinant-human-dihydrofolate-reductase-dhfr-protein-ab87755.html.
Abcam, "ACAD9 Protein (His-DHFR tag) ab127361", Product Datasheet, last accessed Apr. 26, 2016, pp. 1-3, available at: http://www.abcam.com/recombinant-human-acad9-protein-ab127361.html.
Kapoor, M., "How to Isolate Proteins", last accessed Apr. 26, 2016, pp. 1-9, available at: http://www.fgsc.net/neurosporaprotocols/How%20to%20isolate%20proteins%20final.pdf.
International Search Report and Written Opinion dated Apr. 13, 2015 in International Patent Application No. PCT/US2014/060457.
International Preliminary Report on Patentability dated Apr. 28, 2016 in International Patent Application No. PCT/US2014/060457.
Dayhoff, M.O. et al., "A Model of Evolutionary Change in Proteins", In Atlas of Protein Sequence and Structure, vol. 5, supp. 3, Jan. 1978, pp. 345-352.

* cited by examiner

US 10,100,091 B2

FUSION PROTEIN FOR HIV-1 GP120 ANTIGEN DETECTION

CROSS REFERENCE TO RELATED APPLICATION

This application claims the benefit under 35 U.S.C. § 119(e) of U.S. Provisional Application No. 61/890,491, filed Oct. 14, 2013, the content of which is incorporated herein by reference.

FIELD OF THE INVENTION

The present disclosure relates to novel fusion proteins that bind to the HIV-1 gp120 antigen. The present disclosure also relates to nucleic acids, plasmids and host cells that comprise a sequence that encodes the fusion proteins of the disclosure. The fusion proteins of the disclosure can be used in applications to detect the presence of HIV-1 gp120 protein, to detect an HIV-1 infection and to monitor treatment of an HIV-1 infection.

BACKGROUND OF THE INVENTION

Human immunodeficiency virus (HIV) infection is most commonly diagnosed by detecting the appearance of specific antibodies in blood. However, during the earliest stage of infection, rapid replication of HIV makes the immune system dysfunction and for at least several weeks after infection, the immune system cannot produce HIV specific antibodies (Mellors J W, Rinaldo C R Jr, Gupta P, White R M, Todd J A, Kingsley L A (1996) Prognosis in HIV-1 infection predicted by the quantity of virus in plasma. Science 272, 1167-1170). During this period, the virus replicates rapidly, reaching more than a million viral copies per milliliter of blood.

One approach to detecting HIV infection during the early stages of infection is to detect the presence of the HIV virus or its viral components. This can be done using non-direct ELISA methods to detect viral proteins (Gilbert M, Kirihara J, Mills J (1991) Enzyme-linked immunoassay for human immunodeficiency virus type 1 envelope glycoprotein 120. J. Clin. Microbiol. 29, 142-147; Rychert J, Strick D, Bazner S, Robinson J, Rosenberg E (2010) Detection of HIV gp120 in plasma during early HIV infection is associated with increased proinflammatory and immunoregulatory cytokines AIDS Res. Hum. Retroviruses 26, 1139-1145).

One such viral protein is gp120, which is a glycoprotein exposed on the surface of the HIV envelope (Wyatt R, Kwong P D, Desjardins E, Sweet R W, Robinson J, Hendrickson W A, Sodroski J G (1998) The antigenic structure of the HIV gp120 envelope gycoprotein. Nature 393, 705-711; Wyatt, R., and Sodroski, J. (1998). The HIV-1 envelope glycoproteins: fusogens, antigens, and immunogens. Science 280, 1884-1888). The glycoprotein gp120 is anchored to the viral membrane and plays a vital role in virus entry into cells, by binding to CD4 receptors.

ELISA methods for detecting gp120 protein include using pairs of monoclonal antibodies ("capture" and "developer"), which specifically bind to different epitopes of gp120 and do not demonstrate high level of cross-reactivity (Rychert J, Strick D, Bazner S, Robinson J, Rosenberg E (2010) Detection of HIV gp120 in plasma during early HIV infection is associated with increased proinflammatory and immunoregulatory cytokines AIDS Res. Hum. Retroviruses 26, 1139-1145). The average size of these epitopes is 8-10 amino acids, which does not allow for high affinity or efficient binding with the antigen. The sensitivity of this method, thus, is strongly dependent on the antigen-binding efficiency of pair of antibodies, which can vary significantly.

SUMMARY OF THE INVENTION

The present disclosure provides a fusion protein comprising a F23 peptide or a fragment thereof; and an additional peptide portion.

The fusion proteins of the disclosure bind to HIV-1 gp120 protein.

In some embodiments, the F23 peptide or fragment thereof is located at the C terminus of the fusion protein. In other embodiments, the F23 peptide or fragment thereof is located at the N terminus of the fusion protein.

In some embodiments, the F23 peptide or fragment thereof comprises SEQ ID NO:1 or a fragment thereof. In some embodiments, the F23 peptide or fragment thereof is SEQ ID NO:1.

In other embodiments, the F23 peptide or fragment thereof comprises SEQ ID NO:2 or a fragment thereof. In some embodiments, the F23 peptide or fragment thereof is SEQ ID NO:2.

In some embodiments, the additional peptide portion enhances one or more of stability, expression, formation of protein complexes, purification and/or immobilization on solid phase. In certain embodiments, the additional peptide portion enhances stability. In certain embodiments, the additional peptide portion enhances immobilization on solid phase. In certain embodiments, the additional peptide portion enhances stability and immobilization on solid phase.

In some embodiments, the additional peptide portion comprises SEQ ID NO:3 or a fragment thereof. In certain embodiments, the additional peptide portion is SEQ ID NO:3.

In other embodiments, the additional peptide portion comprises SEQ ID NO:4 or a fragment thereof. In certain embodiments, the additional peptide portion is SEQ ID NO:4.

In some embodiments, the additional peptide portion comprises a purification sequence. In certain embodiments, the purification sequence comprises an epitope tag, a FLAG tag, a polyhistidine sequence or a GST fusion. In certain embodiments, the purification sequence is a polyhistidine sequence.

In some embodiments, the additional peptide portion comprises SEQ ID NO:3 or a fragment thereof and a polyhistidine sequence. In certain aspects of this embodiment, the additional peptide portion comprises SEQ ID NO:3 and a polyhistidine sequence. In other embodiments, the additional peptide portion comprises SEQ ID NO:4 or a fragment thereof and a polyhistidine sequence. In certain aspects of this embodiment, the additional peptide portion comprises SEQ ID NO:4 and a polyhistidine sequence.

In some embodiments, the F23 peptide or a fragment thereof comprises SEQ ID NO:1 or a fragment thereof and the additional peptide portion comprises SEQ ID NO:3 or a fragment thereof and a polyhistidine sequence. In certain aspects of this embodiment, the F23 peptide or a fragment thereof comprises SEQ ID NO:1 and the additional peptide portion comprises SEQ ID NO:3 and a polyhistidine sequence. In other embodiments, the F23 peptide or a fragment thereof comprises SEQ ID NO:2 or a fragment thereof and the additional peptide portion comprises SEQ ID NO:3 or a fragment thereof and a polyhistidine sequence. In certain aspects of this embodiment, the F23 peptide or a fragment thereof comprises SEQ ID NO:2 and the additional peptide portion comprises SEQ ID NO:3 and a polyhistidine sequence.

In some embodiments, the F23 peptide or a fragment thereof comprises SEQ ID NO:2 or a fragment thereof and the additional peptide portion comprises SEQ ID NO:3 or a fragment thereof and a polyhistidine sequence. In certain aspects of this embodiment, the F23 peptide or a fragment thereof comprises SEQ ID NO:2 and the additional peptide portion comprises SEQ ID NO:3 and a polyhistidine sequence. In other embodiments, the F23 peptide or a fragment thereof comprises SEQ ID NO:2 or a fragment thereof and the additional peptide portion comprises SEQ ID NO:4 or a fragment thereof and a polyhistidine sequence. In certain aspects of this embodiment, the F23 peptide or a fragment thereof comprises SEQ ID NO:2 and the additional peptide portion comprises SEQ ID NO:4 and a polyhistidine sequence.

The present disclosure also provides an isolated nucleic acid encoding any of the fusion proteins described herein.

The present disclosure also provides a plasmid comprising a nucleic acid encoding any of the fusion proteins described herein.

The present disclosure also provides an isolated host cell transformed with a nucleic acid encoding any of the fusion proteins described herein.

The present disclosure also provides a method for detecting whether HIV-1 gp120 protein may be present in a sample. The method comprises contacting the sample with any of the fusion proteins described herein and detecting the binding of the fusion protein to HIV-1 gp120 protein.

In some embodiments, the detecting step comprises contacting the sample and the fusion protein with a labeled HIV-1 gp120 monoclonal antibody. In certain embodiments, the labeled HIV-1 gp120 monoclonal antibody comprises a fluorescent label. In other embodiments, the labeled gp120 monoclonal antibody comprises a chemiluminescent label.

In some embodiments, the binding of a fusion protein of the disclosure to HIV-1 gp120 protein can be detected by spectroscopic, photochemical, biochemical, immunochemical, chemical or other physical means.

In some embodiments, the sample comprises a cell culture. In some embodiments, the sample is a biological sample. In certain embodiments, the sample is blood.

In some embodiments, the fusion protein used in this method is immobilized on solid phase.

The present disclosure also provides a method of detecting an HIV infection in a subject. The method comprises obtaining a sample from the subject; contacting the sample with any of the fusion proteins described herein, wherein the fusion protein binds to HIV-1 gp120 protein, if present; and detecting the binding of the fusion protein to HIV-1 gp120 protein. Binding of the fusion protein and HIV-1 gp120 protein indicates an HIV infection.

In some embodiments, the detecting step comprises contacting the sample and the fusion protein with a labeled HIV-1 gp120 monoclonal antibody. In certain embodiments, the labeled HIV-1 gp120 monoclonal antibody comprises a fluorescent label. In other embodiments, the labeled gp120 monoclonal antibody comprises a chemiluminescent label.

In some embodiments, the binding of a fusion protein of the disclosure to HIV-1 gp120 protein can be detected by spectroscopic, photochemical, biochemical, immunochemical, chemical or other physical means.

In some embodiments, the sample comprises a cell culture. In some embodiments, the sample is a biological sample. In certain embodiments, the sample is blood.

In some embodiments, the fusion protein used in this method is immobilized on solid phase.

The present disclosure also provides a method of monitoring treatment of an HIV-1 infection in a subject. The method comprises obtaining a first and a second sample from the subject, wherein the first sample is taken from the subject at an earlier time point than the second sample and wherein the second sample is taken from the subject following treatment; separately contacting the first and second sample with any of the fusion proteins described herein, wherein the fusion protein binds to HIV-1 gp120 protein, if present; separately detecting the binding of the fusion protein to HIV-1 gp120 protein in the first and second sample; and comparing the fusion protein-HIV-1 gp120 protein binding of the first and second samples. An increase in the fusion protein-HIV-1 gp120 protein binding in the second sample relative to the first sample indicates inefficacy of the treatment of the HIV-1 infection in the subject and a decrease in the fusion protein-HIV-1 gp120 protein binding in the second sample relative to the first sample indicates efficacy of the treatment.

In some embodiments, the detecting step comprises contacting the sample and the fusion protein with a labeled HIV-1 gp120 monoclonal antibody. In certain embodiments, the labeled HIV-1 gp120 monoclonal antibody comprises a fluorescent label. In other embodiments, the labeled gp120 monoclonal antibody comprises a chemiluminescent label.

In some embodiments, the binding of a fusion protein of the disclosure to HIV-1 gp120 protein can be detected by spectroscopic, photochemical, biochemical, immunochemical, chemical or other physical means.

In some embodiments, the sample comprises a cell culture. In some embodiments, the sample is a biological sample. In certain embodiments, the sample is blood.

In some embodiments, the fusion protein used in this method is immobilized on solid phase.

In some embodiments, the subject is human.

The present disclosure also provides a kit comprising any of the fusion proteins described herein. In some embodiments, the kit further comprises any of the labeled gp120 monoclonal antibodies described herein.

The present disclosure also provides a diagnostic device comprising any of the fusion proteins described herein. In some embodiments, the diagnostic device further comprises any of the labeled gp120 monoclonal antibodies described herein. In some embodiments, the diagnostic device detects binding of the fusion protein to HIV-1 gp120 protein by spectroscopic, photochemical, biochemical, immunochemical, chemical or other physical means.

BRIEF DESCRIPTION OF THE FIGURES

FIG. 5A shows detection using a F23 fusion protein of the disclosure. FIG. 5B shows detecting using a control with BL21 cell lysate.

FIG. 6A shows detection of gp120 protein using dot blot. Dot 1, reaction with 100 pg of gp120 protein in 1 mL human serum; dot 2, reaction with 10 pg of gp120 protein in 1 mL human serum; dot 3, reaction with 1 pg of gp120 protein in 1 mL human serum; dot 4, reaction without gp120 protein in 1 mL human serum. FIG. 6B shows the relative intensity of each reaction.

DETAILED DESCRIPTION OF THE INVENTION

Figure 1:
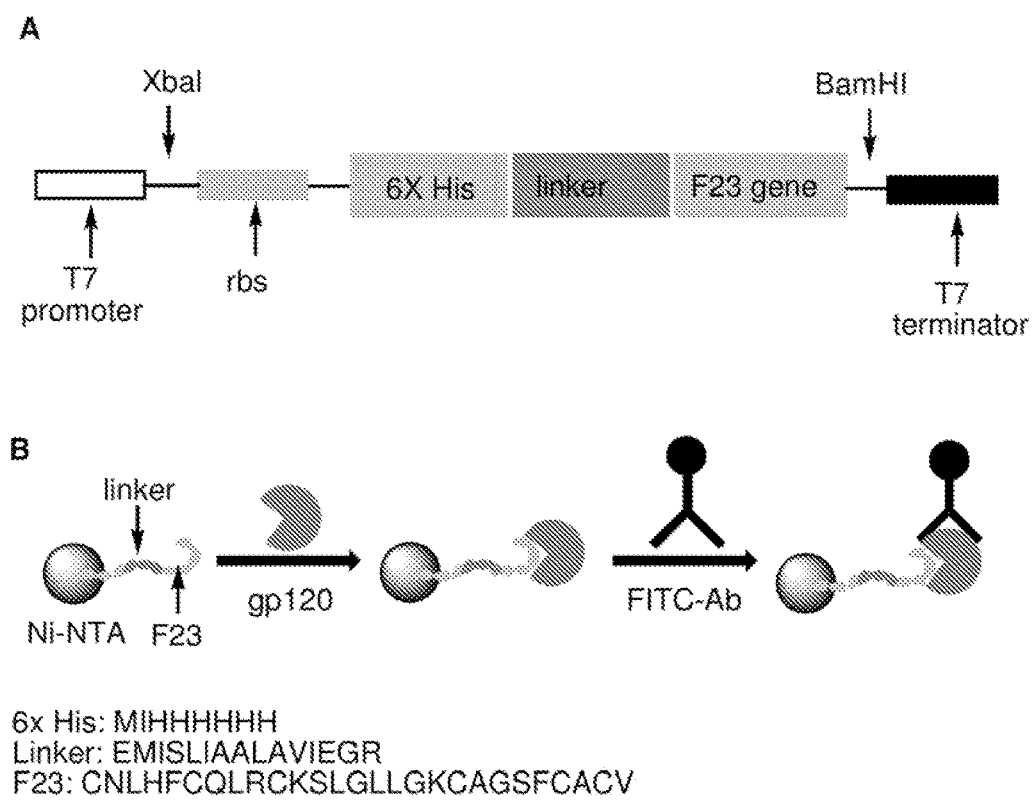
FIG. 1A is a gene construct for the in vitro expression of a F23 fusion protein of the disclosure.
FIG. 1B shows a strategy for detecting HIV-1 gp120 protein using a F23 fusion protein of the disclosure.

The disclosure includes the following:
(1.) A fusion protein comprising a F23 peptide or a fragment thereof; and an additional peptide portion.
(2.) The fusion protein of the above (1.), wherein the fusion protein binds to HIV-1 gp120 protein.
(3.) The fusion protein of the above (1.), wherein the F23 peptide or fragment thereof is located at the C terminus of the fusion protein.
(4.) The fusion protein of the above (1.), wherein the F23 peptide or fragment thereof comprises SEQ ID NO:1 or a fragment thereof.
(5.) The fusion protein of the above (1.), wherein the F23 peptide or fragment thereof is SEQ ID NO:1.
(6.) The fusion protein of the above (1.), wherein the F23 peptide or fragment thereof comprises SEQ ID NO:2 or a fragment thereof.
(7.) The fusion protein of the above (1.), wherein the F23 peptide or fragment thereof is SEQ ID NO:2.
(8.) The fusion protein of the above (1.), wherein the additional peptide portion enhances one or more of stability, expression, formation of protein complexes, purification and/or immobilization on solid phase.
(9.) The fusion protein of the above (8.), wherein the additional peptide portion enhances stability.
(10.) The fusion protein of the above (1.), wherein the additional peptide portion comprises SEQ ID NO:3 or a fragment thereof.
(11.) The fusion protein of the above (1.), wherein the additional peptide portion is SEQ ID NO:3.
(12.) The fusion protein of the above (1.), wherein the additional peptide portion comprises SEQ ID NO:4 or a fragment thereof.
(13.) The fusion protein of the above (1.), wherein the additional peptide portion is SEQ ID NO:4.
(14.) The fusion protein of the above (1.), wherein the additional peptide portion comprises a purification sequence.
(15.) The fusion protein of the above (14.), wherein the purification sequence comprises an epitope tag, a FLAG tag, a polyhistidine sequence or a GST fusion.
(16.) The fusion protein of the above (15.), wherein the purification sequence is a polyhistidine sequence.
(17.) The fusion protein of the above (1.), wherein the additional peptide portion comprises SEQ ID NO:3 or a fragment thereof and a polyhistidine sequence.
(18.) The fusion protein of the above (1.), wherein the additional peptide portion comprises SEQ ID NO:4 or a fragment thereof and a polyhistidine sequence.
(19.) The fusion protein of the above (1.), wherein the F23 peptide or a fragment thereof comprises SEQ ID NO:1 or a fragment thereof and the additional peptide portion comprises SEQ ID NO:3 or a fragment thereof and a polyhistidine sequence.
(20.) The fusion protein of the above (1.), wherein the F23 peptide or a fragment thereof comprises SEQ ID NO:1 or a fragment thereof and the additional peptide portion comprises SEQ ID NO:4 or a fragment thereof and a polyhistidine sequence.
(21.) The fusion protein of the above (1.), wherein the F23 peptide or a fragment thereof comprises SEQ ID NO:2 or a fragment thereof and the additional peptide portion comprises SEQ ID NO:3 or a fragment thereof and a polyhistidine sequence.
(22.) The fusion protein of the above (1.), wherein the F23 peptide or a fragment thereof comprises SEQ ID NO:2 or a fragment thereof and the additional peptide portion comprises SEQ ID NO:4 or a fragment thereof and a polyhistidine sequence.
(23.) An isolated nucleic acid encoding a fusion protein of any of the above (1.) to (22.).
(24.) A plasmid comprising a nucleic acid encoding the fusion protein of any of the above (1.) to (22.).
(25.) An isolated host cell transformed with a nucleic acid encoding the fusion protein of any of the above (1.) to (22.).
(26.) A method for detecting whether HIV-1 gp120 protein may be present in a sample comprising:
(a) contacting the sample with the fusion protein of any of the above (1.) to (22.), wherein the fusion protein binds to HIV-1 gp120 protein, if present; and
(b) detecting the binding of the fusion protein to HIV-1 gp120 protein.
(27.) The method of the above (26.), wherein the detecting step comprises contacting the sample and the fusion protein with a labeled HIV-1 gp120 monoclonal antibody.
(28.) The method of the above (27.), wherein the labeled HIV-1 gp120 monoclonal antibody comprises a fluorescent label.
(29.) The method of the above (27.), wherein the labeled gp120 monoclonal antibody comprises a chemiluminescent label.
(30.) The method of the above (26.), wherein the sample comprises a cell culture.
(31.) The method of the above (26.), wherein the sample is a biological sample.
(32.) The method of the above (31.), wherein the sample is blood.
(33.) The method of the above (26.), wherein the fusion protein is immobilized on solid phase.
(34.) A method of detecting an HIV infection in a subject comprising:
(a) obtaining a sample from the subject;
(b) contacting the sample with the fusion protein of any of the above (1.) to (22.), wherein the fusion protein binds to HIV-1 gp120 protein, if present; and
(c) detecting the binding of the fusion protein to HIV-1 gp120 protein, wherein binding of the fusion protein and HIV-1 gp120 protein indicates an HIV infection.

(35.) The method of the above (34.), wherein the detecting step comprises contacting the sample and the fusion protein with a labeled HIV-1 gp120 monoclonal antibody.

(36.) The method of the above (35.), wherein the labeled HIV-1 gp120 monoclonal antibody comprises a fluorescent label.

(37.) The method of the above (35.), wherein the labeled gp120 monoclonal antibody comprises a chemiluminescent label.

(38.) The method of the above (34.), wherein the sample is blood.

(39.) The method of the above (34.), wherein the subject is human.

(40.) The method of the above (34.), wherein the fusion protein is immobilized on solid phase.

(41.) A method of monitoring treatment of an HIV-1 infection, comprising:
(a) obtaining a first and a second sample from a subject, wherein the first sample is taken from the subject at an earlier time point than the second sample and wherein the second sample is taken from the subject following treatment;
(b) separately contacting the first and second sample with the fusion protein of any of the above (1.) to (22.), wherein the fusion protein binds to HIV-1 gp120 protein, if present;
(c) separately detecting the binding of the fusion protein to HIV-1 gp120 protein in the first and second sample; and
(d) comparing the fusion protein-HIV-1 gp120 protein binding of the first and second samples.

(42.) The method of the above (41.), wherein the detecting step comprises contacting the sample and the fusion protein with a labeled HIV-1 gp120 monoclonal antibody.

(43.) The method of the above (42.), wherein the labeled HIV-1 gp120 monoclonal antibody comprises a fluorescent label.

(44.) The method of the above (42.), wherein the labeled gp120 monoclonal antibody comprises a chemiluminescent label.

(45.) The method of the above (41.), wherein the sample is blood.

(46.) The method of the above (41.), wherein the subject is human.

(47.) The method of the above (41.), wherein the fusion protein is immobilized on solid phase.

(48.) A kit for detecting the presence or absence of HIV-1 gp protein in a sample, wherein the kit comprises the fusion protein of any of the above (1.) to (22.).

(49.) A kit for detecting an HIV infection in a subject, wherein the kit comprises the fusion protein of any of the above (1.) to (22.).

(50.) A kit for monitoring treatment of an HIV-1 infection in a subject, wherein the kit comprises the fusion protein of any of the above (1.) to (22.).

(51.) A diagnostic device comprising the fusion protein of any of the above (1.) to (22.).

(52.) The diagnostic device of the above (51.) further comprising a labeled gp120 monoclonal antibody.

In order that the disclosure herein described may be fully understood, the following detailed description is set forth. Unless defined otherwise, all technical and scientific terms used herein have the same meaning as those commonly understood by one of ordinary skill in the art to which this disclosure belongs. Although methods and materials similar or equivalent to those described herein can be used in the practice or testing of the present disclosure, suitable methods and materials are described below. The materials, methods and examples are illustrative only, and are not intended to be limiting. All publications, patents and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

The term "a" or "an" may mean more than one of an item.

The terms "and" and "or" may refer to either the conjunctive or disjunctive and mean "and/or".

The term "about" means within plus or minus 10% of a stated value. For example, "about 100" would refer to any number between 90 and 110.

Fusion Proteins, Nucleic Acids, Plasmids, and Host Cells

The present disclosure provides a fusion protein comprising two components, namely, a F23 peptide or a fragment thereof; and an additional peptide portion.

As used herein, the term "F23 peptide" refers to a peptide that mimics CD4.

The term "fragment," as used herein, refers to an amino acid sequence that is shorter than the peptide from which it is derived, and that retains the activity substantially similar to that of the original peptide. Such a fragment is at least two amino acids in length.

In some embodiments, the F23 peptide or fragment thereof binds to HIV-1 gp120 protein.

In some embodiments, the F23 peptide or fragment thereof is located at the C terminus of the fusion protein. In other embodiments, the F23 peptide or fragment thereof is located at the N terminus of the fusion protein.

In some embodiments, the F23 peptide comprises the sequence: CNLHFCQLRCKSLGLLGKCAGSFCACV (SEQ ID NO:1) or a fragment thereof, or a sequence having at least 70% or, more preferably, 80% or 90% amino acid sequence homology with the amino acid sequence of SEQ ID NO:1 and binds to HIV-1 gp120 protein. As used herein, a percentage "homology" between two amino acid sequences indicates the percentage of amino acid residues that are identical or similar between the sequences and, as used herein, "similar" residues are "conservative substitutions" which fulfill the criteria defined for an "accepted point mutation" in Dayhoff et al. (1978), Atlas of Protein Sequence and Structure Vol. 5 (Suppl. 3), pp. 354-352, Natl. Biomed. Res. Found., Washington, D.C. As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) Ala, Pro, Gly, Glu, Asp, Gln, Asn, Ser, Thr; (2) Cys, Ser, Tyr, Thr; (3) Val, Ile, Leu, Met, Ala, Phe; (4) Lys, Arg, His; and (5) Phe, Tyr, Trp, His. In some aspects of this embodiment, the F23 peptide is SEQ ID NO:1.

In some aspects of this embodiment, the F23 peptide comprises a fragment of SEQ ID NO:1 having from about 2 to about 26 amino acids. In some aspects, the F23 peptide comprises a fragment of SEQ ID NO:1 having from about 10 to about 26 amino acids. In other aspects, the F23 peptide comprises a fragment of SEQ ID NO:1 having from about 15 to about 26 amino acids.

In other embodiments, the F23 peptide comprises the sequence: KKVVLGKKGD TVELTCTASG KKSIGFHWKN SNGIKILGNG GSFLTKGPSK LNDRADSRRS LWDGGNFPLI IKNLKIEDSD TYICEVEDGK EEVGLL- VFGL TRANSDTHLLG GGSLTLTLES (SEQ ID NO:2) or a fragment thereof or a sequence having at least 70% or, more preferably, 80% or 90% amino acid sequence homology with the amino acid sequence of SEQ ID NO:2 and binds to HIV-1 gp120 protein. In some aspects of this embodiment, the F23 peptide is SEQ ID NO:2.

In some aspects of this embodiment, the F23 peptide comprises a fragment of SEQ ID NO:2 having from about 2 to about 119 amino acids. In some aspects, the F23 peptide comprises a fragment of SEQ ID NO:2 having from about 5 to about 119 amino acids. In other aspects, the F23 peptide comprises a fragment of SEQ ID NO:2 having from about 10 to about 119 amino acids.

The second component of the fusion protein of the disclosure is an additional peptide portion. In some embodiments, the additional peptide portion enhances one or more of stability, expression, formation of protein complexes, purification and/or immobilization on solid phase. In certain embodiments, the additional peptide portion enhances stability. In other embodiments, it enhances purification. In yet other embodiments, it enhances immobilization on solid phase. In some embodiments, the additional peptide portion enhances stability, purification and immobilization on solid phase.

In some embodiments, the additional peptide portion comprises the sequence: EMISLIAALAVIEGR (SEQ ID NO:3) or a fragment thereof a sequence having at least 70% or, more preferably, 80% or 90% amino acid sequence homology with the amino acid sequence of SEQ ID NO:3 and enhances stability.

In some aspects of this embodiment, the additional peptide portion comprises SEQ ID NO:3. In some aspects of this embodiment, the additional peptide portion comprises a fragment of SEQ ID NO:3 having from about 10 to about 14 amino acids. In some aspects, the additional peptide portion comprises a fragment of SEQ ID NO:3 having from about 11 to about 14 amino acids. In other aspects, the additional peptide portion comprises a fragment of SEQ ID NO:3 having from about 12 to about 14 amino acids.

In other embodiments, the additional peptide portion comprises the sequence: EMISLIAALAV DRVIGMENAM PWNLPADLAW FKRNTLNKPV IMGRHTWESI (SEQ ID NO:4) or a fragment thereof, or a sequence having at least 70% or, more preferably, 80% or 90% amino acid sequence homology with the amino acid sequence of SEQ ID NO:4 and enhances stability.

In some aspects of this embodiment, the additional peptide portion comprises SEQ ID NO:4. In some aspects of this embodiment, the additional peptide portion comprises a fragment of SEQ ID NO:4 having from about 10 to about 50 amino acids. In some aspects, the additional peptide portion comprises a fragment of SEQ ID NO:4 having from about 20 to about 45 amino acids. In other aspects, the additional peptide portion comprises a fragment of SEQ ID NO:4 having from about 30 to about 40 amino acids.

In some embodiments, the additional peptide portion comprises a purification sequence. Useful purification sequences include, but are not limited to, those comprising an epitope tag, a FLAG tag, a polyhistidine sequence, a GST fusion, CBP, CYD (covalent yet dissociable NorpD peptide), Strep tag, HPC (heavy chain of protein C) peptide tags. In certain embodiments, the purification sequence is a polyhistidine sequence.

In some embodiments, the additional peptide portion comprises SEQ ID NO:3 or fragment thereof and a polyhistidine sequence. In embodiments in which the additional peptide portion comprises a fragment of SEQ ID NO:3, the fragment has from about 10 to about 14 amino acids. In some aspects of this embodiment, the fragment has from about 11 to about 14 amino acids. In other aspects, the fragment has from about 12 to about 14 amino acids.

In other embodiments, the additional peptide portion comprises SEQ ID NO:4 or a fragment thereof and a polyhistidine sequence. In embodiments in which the additional peptide portion comprises a fragment of SEQ ID NO:4, the fragment has from about 10 to about 50 amino acids. In some aspects of this embodiment, the fragment has from about 20 to about 45 amino acids. In other aspects, the fragment has from about 30 to about 40 amino acids.

In one embodiment, the present disclosure provides a fusion protein comprising a F23 peptide or a fragment thereof and an additional peptide portion, wherein the F23 peptide or a fragment thereof comprises SEQ ID NO:1 or a fragment thereof and the additional peptide portion comprises SEQ ID NO:3 or a fragment thereof and a polyhistidine sequence.

In a second embodiment, the present disclosure provides a fusion protein comprising a F23 peptide or a fragment thereof and an additional peptide portion, wherein the F23 peptide or a fragment thereof comprises SEQ ID NO:2 or a fragment thereof and the additional peptide portion comprises SEQ ID NO:3 or a fragment thereof and a polyhistidine sequence.

In a third embodiment, the present disclosure provides a fusion protein comprising a F23 peptide or a fragment thereof and an additional peptide portion, wherein the F23 peptide or a fragment thereof comprises SEQ ID NO:1 or a fragment thereof and the additional peptide portion comprises SEQ ID NO:4 or a fragment thereof and a polyhistidine sequence.

In a fourth embodiment, the present disclosure provides a fusion protein comprising a F23 peptide or a fragment thereof and an additional peptide portion, wherein the F23 peptide or a fragment thereof comprises SEQ ID NO:2 or a fragment thereof and the additional peptide portion comprises SEQ ID NO:4 or a fragment thereof and a polyhistidine sequence.

In any of the four preceding embodiments in which the fusion protein comprises a fragment of the F23 peptide or the additional peptide portion, the fragment thereof may be any of the fragments described above.

The fusion protein of the present disclosure binds to HIV-1 gp120 protein. This binding can be used in methods to detect HIV-1 gp120, to detect an HIV infection and to monitor treatment of an HIV infection, as discussed below.

The fusion proteins of the present disclosure may be prepared by chemical synthesis, in vivo expression or in vitro expression. In some embodiments, the fusion proteins are prepared by in vivo expression.

The fusion protein may be expressed in vivo according to standard techniques. In some embodiments, the temperature at which expression is induced is about 30° C. In some embodiments, the duration of expression is about 30 min.

The present disclosure also provides an isolated nucleic acid encoding any of the fusion proteins described herein.

As used herein, the term "isolated" when used to refer to a product (e.g., a peptide, protein, DNA, host cell, etc.), refers to a non-naturally occurring product that is markedly different in structure from a naturally occurring product.

The present disclosure also provides a plasmid comprising a nucleic acid encoding any of the fusion proteins described herein.

The present disclosure also provides an isolated host cell transformed with a nucleic acid encoding any of the fusion proteins described herein.

The term "host cell", as used herein refers to a cell which has been transduced, infected, transfected or transformed with a vector. The vector may be a plasmid, a viral particle, a phage, etc. The culture conditions, such as temperature, pH and the like, are those previously used with the host cell selected for expression, and will be apparent to those skilled in the art. It will be appreciated that the term "host cell" refers to the original transduced, infected, transfected or transformed cell and progeny thereof.

The host cell of the present disclosure may be prepared by conventional techniques well known to those of ordinary skill in the art.

Methods of Use and Kits

The present disclosure also provides a method for detecting whether HIV-1 gp120 protein may be present in a sample. The method comprises: (a) contacting the sample with any of the fusion proteins described herein, wherein the fusion protein binds to HIV-1 gp120 protein, if present; and (b) detecting the binding of the fusion protein to HIV-1 gp120 protein.

The present disclosure also provides a method of detecting an HIV infection in a subject. The method comprises (a) obtaining a sample from the subject; (b) contacting the sample with any of fusion proteins described herein, wherein the fusion protein binds to HIV-1 gp120 protein, if present; and (c) detecting the binding of the fusion protein to HIV-1 gp120 protein, wherein binding of the fusion protein and HIV-1 gp120 protein indicates an HIV infection.

The present disclosure also provides a method of monitoring treatment of an HIV-1 infection. The method comprises (a) obtaining a first and a second sample from a subject, wherein the first sample is taken from the subject at an earlier time point than the second sample and wherein the second sample is taken from the subject following treatment; (b) separately contacting the first and second sample with any of fusion proteins described herein, wherein the fusion protein binds to HIV-1 gp120 protein, if present; (c) separately detecting the binding of the fusion protein to HIV-1 gp120 protein in the first and second sample; and (d) comparing the fusion protein-HIV-1 gp120 protein binding of the first and second samples. An increase in the fusion protein-HIV-1 gp120 protein binding in the second sample relative to the first sample indicates inefficacy of the treatment of the HIV-1 infection in the subject and a decrease in the fusion protein-HIV-1 gp120 protein binding in the second sample relative to the first sample indicates efficacy of the treatment.

In all of the methods described herein, the sample may comprise a cell culture. The sample may be a biological sample. In some aspects of this embodiment, the sample is selected from the group consisting of tissue, blood, saliva, plasma, serum, or other fluid from a biological source. In some aspects, the sample is blood.

The term "subject", as used herein, means an animal, preferably a mammal, and most preferably a human.

In all of the methods described herein, various assay protocols may be employed for detecting the binding of the fusion protein to HIV-1 gp120 protein. Of particular interest is detecting binding using a labeled HIV-1 gp120 monoclonal antibody. As used herein, the term "labeled" refers broadly to a moiety that is detectable by spectroscopic, photochemical, biochemical, immunochemical, chemical, or other physical means. The labeled HIV-1 gp120 monoclonal antibody used in the detecting step includes, but is not limited to, an antibody comprising a fluorescent label, a chemiluminescent label, a radiolabel, enzyme, enzyme substrate, cofactor or inhibitor, particles, e.g., magnetic particles, combinations of ligands and receptors, e.g., biotin and avidin, or the like. In some aspects of this embodiment, the labeled HIV-1 gp120 monoclonal antibody is FITC labeled gp120 specific monoclonal antibody. In other aspects, the labeled HIV-1 gp120 monoclonal antibody is anti-HIV gp120 antibody conjugated with peroxidase.

In assay protocols involving the use of a labeled HIV-1 gp120 monoclonal antibody, binding of the labeled antibody to the fusion protein-HIV-1 gp120 complex results in being able to discriminate between the label bound to the complex and unbound label (or label not involved in the complex). Such assay protocols are known in the art.

Depending upon the nature of the assay, the sample may be pretreated by dilution into an assay medium, which will usually be an aqueous buffered medium employing one of a variety of buffers, such as phosphate, tris, or the like. Usually the pH will be in the range of about 6 to about 9. The sample will then be combined with a fusion protein of the disclosure in accordance with appropriate assay protocol and for sufficient time to allow for binding. Usually the combination step is followed by washes to minimize non-specific binding. At the end of the procedure, the label will be detected in accordance with conventional methods.

In all of the methods described herein, the fusion protein may be immobilized on solid phase. As used herein, "solid phase" and "solid support" refer broadly to any material that provides a solid or semi-solid structure with which another material can be attached including, but not limited to, smooth supports (e.g., metal, glass, plastic, silicon, and ceramic surfaces) as well as textured and porous materials.

The solid phase support may be, in some embodiments, a bead, plate, matrix, polymer, membrane, test tube, sheet, culture dish, test strip, chromatographic surface, e.g., paper, cellulose, silica gel or the like. In some aspects of this embodiment, the solid phase support is a bead, such as Ni-NTA magnetic agarose beads. In other embodiments, the solid support is a membrane, such as a nitrocellulose membrane.

Methods for immobilizing the fusion protein are known in the art and will vary depending on the solid support chosen.

The present disclosure also provides a kit comprising any of fusion proteins described herein. The kit may further comprise a labeled HIV-1 gp120 monoclonal antibody as described herein. In some embodiments, the fusion protein is immobilized on solid phase.

The kit can be used in any of the methods described herein.

The present disclosure also provides a diagnostic device comprising any of the fusion proteins described herein. In some embodiments, the diagnostic device further comprises any of the labeled gp120 monoclonal antibodies described herein. In some embodiments, the diagnostic device detects binding of the fusion protein to HIV-1 gp120 protein by spectroscopic, photochemical, biochemical, immunochemical, chemical or other physical means.

The device can be used in any of the methods described herein.

In order that this disclosure be more fully understood, the following examples are set forth. These examples are for the purpose of illustration only and are not to be construed as limiting the scope of the disclosure in any way.

EXAMPLES

Materials and Methods
Construction of F23 Peptide

The gene of fusion F23 peptide containing the His6-tag, a linker and the F23 was constructed using two synthesized oligonucleotides (IDT, USA): a forward oligonucleotide (5'-GAT ATA CAT ATG ATC CAC CAT CAC CAC CAT CAC GAA ATG ATC AGT CTG ATT GCG GCG TTA GCG GTA ATC GAA GGT CGT TGT AAC TTA CAC TTC-3') and a backward oligonucleotide (5'-CGC GGA TCC TTA TAC GCA CGC ACA ACT GCC GGC GCA TTT TCC GAG TAA ACC CAA GCT CTT ACA GCG GAG TTG GCA GAA GTG TAA GTT ACA ACG ACC-3') containing restriction site for BamH I (New England BioLabs, USA) at the C-terminus of F23 peptide gene. After annealing, the oligonucleotides were elongated by Taq DNA polymerase (New England BioLabs, USA) to obtain the double-strands DNA fragment, which was purified with QIAquick gel extraction kit (Qiagen, USA). This double-stranded DNA was elongated via a PCR reaction using two synthetic primers (IDT, USA): a forward primer (5'-CCC TCT AGA AAT AAT TTT GTT TAA CTT TAA GAA GGA GAT ATA CAT ATG GAG AAA AAA ATC-3') containing a restriction site for Xba I (New England BioLabs, USA) at the 5'-end and a backward primer (5'-CGC GGA TCC TTA TAC GCA CGC-3'). After purification with QIAquick gel extraction kit, the obtained double-stranded DNA was digested with Xba I and BamH I and inserted into pET16b vector. The newly constructed plasmid was amplified in DH5a cells.

In Vitro Expression of F23 Peptide

The in vitro expression of a fusion F23 peptide of the disclosure was carried out in a cell free expression system (Duca M, Chen S, Hecht S M (2008) Aminoacylation of transfer RNAs with one and two amino acids. Methods 44, 87-99; Chen S, Hecht S M (2008) Synthesis of pdCpAs and transfer RNAs activated with derivatives of aspartic acid and cysteine. Bioorg. Med. Chem. 16, 9023-9031; Chen S, Fahmi N, Nangreave R C, Mehellou Y, Hecht S M (2012) Synthesis of pdCpAs and transfer RNAs activated with thiothreonine and derivatives. Bioorg. Med. Chem. 20, 2679-2689; Chen S, Wang L, Fahmi N, Benkovic S J, Hecht S M (2012) Two pyrenylalanines in dihydrofolate reductase form an excimer enabling the study of protein dynamics. J. Am. Chem. Soc. 134, 18883-18885; and Nangreave R C, Dedkova L M, Chen S, Hecht S M (2011) A new strategy for the synthesis of bisaminoacylated tRNAs. Org. Lett. 13, 4906-4909). The reaction mixture (300 µL total volume) contained 30 µg of plasmid DNA, 120 µL of premix (35 mM Tris-acetate, pH 7.0, 190 mM potassium glutamate, 30 mM ammonium acetate, 2.0 mM dithiothreitol, 11 mM magnesium acetate, 20 mM phospho(enol)pyruvate, 0.8 mg/mL of $E.$ $coli$ tRNA, 0.8 mM IPTG, 20 mM ATP and GTP, 5 mM CTP and UTP and 4 mM cAMP), 100 µM of each of the 20 amino acids, 30 µCi of [$^{35}$S]-L-methionine, 10 µg/µL rifampicin, and 90 µL of S-30 extract from $E.$ $coli$ strain BL21 (DE3). The mixture was incubated at 20-35° C. An aliquot containing 3 µL of reaction mixture was removed from each sample at a predetermined time, treated with 5 µL of loading buffer, and heated at 90° C. for 2 min. The samples were analyzed by 16.5% SDS-PAGE at 100 V for 2 h. The gel was scanned with phosphorimager.

In Vivo Expression of F23 Peptide

One colony of $E.$ $coli$ strain BL21(DE3) cell containing a fusion F23 peptide gene of the disclosure was cultured in 5 mL of LB medium at 37° C. until OD600 about 0.8. Then, 5 µL of 1M isopropylthio-β-galactoside (IPTG) was added to the culture medium and incubated at 30° C. An aliquot containing 300 µL of LB medium was taken out every 15 min and analyzed by 16.5% SDS-PAGE at 100 V for 2 h. The gel was stained with Coomassie blue R-250.

Mass Spectra Assay of Fusion F23 Peptide

The Coomassie blue stained fusion F23 peptide was cut from the SDS-PAGE gel and suspended in 500 µL of 0.1 M ammonium bicarbonate at room temperature for 1 h (Maini R, Nguyen D T, Chen S, Dedkova L M, Chowdhury S R, Alcala-Torano R, Hecht S M (2013) Incorporation of β-amino acids into dihydrofolate reductase by ribosomes having modifications in the peptidyltransferase center. Bioorg. Med. Chem. 21, 1088-1096). The wash was discarded. 200 µL of 0.1 M DTT was added to the gel pieces and incubated at room temperature for 30 min. After washing three times with 200 µL of 0.1 M ammonium bicarbonate, 200 µL of 0.01 M iodoacetamide was added to the gel pieces and incubated at room temperature for 30 min in the dark. Next, the gel pieces were washed with 200 µL of 1:1 mixture of acetonitrile and 0.1 M of ammonium bicarbonate following by 100 µL of 100% acetonitrile. After drying under vacuum for 5 min, 60 µL of 20 ng/µL trypsin in 25 mM ammonium bicarbonate (pH 8.5), or Glu-C in 50 mM ammonium bicarbonate (pH 7.8) was added to the gel pieces. The digestion was incubated at 37° C. overnight. Digested peptides were extracted with 100 µL of 6:4 mixture of acetonitrile and 0.1% trifluoroacetic acid, and analyzed with MALDI mass spectroscopy.

Trapping HIV-1 gp120 Protein for Detection

The BL21(DE3) cell pellet from 1 mL of the in vivo expression of reaction was resuspended in 100 µL of 50 mM Tris-HCl, pH 7.2, containing 100 mM NaCl. The BL21 (DE3) cell without any plasmid was used as the negative control. The cells were lysed with ultrasonic (15 second for 6 times). After centrifugation at 15,000 g for 30 min, 10 µL of Ni-NTA magnetic agarose beads (Qiagen, USA) was added to the lysate. The beads were washed three times with 100 µL of 50 mM Tris-HCl, pH 7.2, containing 100 mM NaCl, 10 mM imidazole and 1% BSA, followed by the addition 1 µg of gp120 protein (Fitzgerald Industries International Inc, USA). The reaction mixture was incubated with shaking at 4° C. for 2 h. The Ni-NTA magnetic agarose beads were washed three times with 100 µL of 50 mM Tris-HCl, pH 7.2, containing 100 mM NaCl, 10 mM imidazole and 1% BSA. Then the beads were incubated with shaking at 4° C. for 2 h in 100 µL of 50 mM Tris-HCl, pH 7.2, containing 100 mM NaCl, 10 mM imidazole, 1% BSA and 1 µg of fluorescein isothiocyanate (FITC) labeled HIV-1 gp120 antibody (Fitzgerald Industries International Inc, USA). After washing three times with 100 µL of 50 mM Tris-HCl, pH 7.2, containing 100 mM NaCl, 10 mM imidazole and 1% BSA, the beads were monitored with a fluorescent microscope.

Dot Blot Assay to Detect gp120 Protein in Human Serum

The Ni-NTA purified fusion F23 peptide (1 µL, 5 ng) was spotted on the nitrocellulose membrane (Sulimenko T, Draber P (2004) A fast and simple dot-immunobinding assay for quantification of mouse immunoglobulins in hybridoma culture supernatants. J. Immunol. Methods 289, 89-95). The membrane was air dried for 30 min. at room temperature and transferred into a 24-well plate. The loaded membranes were blocked with 1 mL of 2% fat-free milk in TBST buffer (20 mM Tris-HCl, pH 7.5, 150 mM NaCl, 0.05% Tween 20) for 1 h. After washing three times with 1 mL of TBST buffer, 1 mL of 10-fold diluted human serum (Sigma, USA) containing different amount HIV-1 gp120 protein (Fitzgerald Industries International Inc, USA) was added to the membranes and incubated at room temperature for 1 h. After washing three times with 1 mL of TBST buffer, the membranes were added 1 mL of 1/1000 diluted HRP-conjugated HIV-1 gp120 antibody (Fitzgerald Industries International Inc, USA) and incubated at room temperature for 1 h. After washing three times with 1 mL of TBST buffer, the membranes were treated with chemiluminiscence reagents (Thermo Scien- Results and Discussion Construction of F23 Peptide CD4 is a large protein, containing four immunoglobulin domains (D1 to D4) that are exposed on the extracellular surface of the T cell and responsible for interaction with domain to interact with different regulative molecules in human blood. Only three regions (31-35; 40-48 and 58-64 residues) are the most important for gp120 binding (Lee K-H, Kwon Y-C, Yoo S J, Kim D-M (2010) Ribosomal synthesis and in situ isolation of peptide molecules in a cell-free translation system. Protein Expr. Purif. 71, 16-20; and Loose C R, Langer R S, Stephanopoulos G N (2007) Optimization of protein fusion partner length for maximizing in vitro translation of peptides. Biotechnol. Prog. 23, 444-451). The 27-amino acid-length F23 peptide is an efficiently mimic of CD4 domain to study CD4-gp120 binding (Huang C C, Stricher F, Martin L, Decker J M, Majeed S, Barthe P, Hendrickson W A, Robinson J, Roumestand C, Sodroski J, Wyatt R, Shaw G M, Vita C, Kwong P D (2005) Scorpion-toxin mimics of CD4 in complex with human immunodeficiency virus gp120: crystal structures, molecular mimicry, and neutralization breadth. Structure 13, 755-768).

To avoid complicated chemical synthesis of the F23 peptide, a new plasmid, pET16bF23, was constructed to express the peptide using a ribosome. E. coli dihydrofolate reductase (DHFR) has been used as a protein model to study enzyme function and dynamics (Duca M, Chen S, Hecht S M (2008) Aminoacylation of transfer RNAs with one and two amino acids. Methods 44, 87-99; Chen S, Hecht S M (2008) Synthesis of pdCpAs and transfer RNAs activated with derivatives of aspartic acid and cysteine. Bioorg. Med. Chem. 16, 9023-9031; Chen S, Fahmi N, Nangreave R C, Mehellou Y, Hecht S M (2012) Synthesis of pdCpAs and transfer RNAs activated with thiothreonine and derivatives. Bioorg. Med. Chem. 20, 2679-2689; Chen S, Wang L, Fahmi N, Benkovic S J, Hecht S M (2012) Two pyrenylalanines in dihydrofolate reductase form an excimer enabling the study of protein dynamics. J. Am. Chem. Soc. 134, 18883-18885; and Nangreave R C, Dedkova L M, Chen S, Hecht S M (2011) A new strategy for the synthesis of bisaminoacylated tRNAs. Org. Lett. 13, 4906-4909). In previous work, it was found that the peptide, containing the first 15 amino acids of DHFR, could be synthesized in vitro with and demonstrated high stability (data not published) while a shorter peptide, containing the first 9 amino acids of DHFR, was quickly digested. Thus, to stabilize the F23 peptide, a fusion gene, having a 15 amino acid length linker derived from DHFR was designed. As shown in FIG. 1A, the obtained plasmid (pET16bF23) included the sequence for a His-tag, a 15 amino acid length linker and the F23. The sequence for six N-terminal histidine residues was inserted for purification and solid binding.

In Vitro Expression of Fusion F23 Peptide

Figure 2:
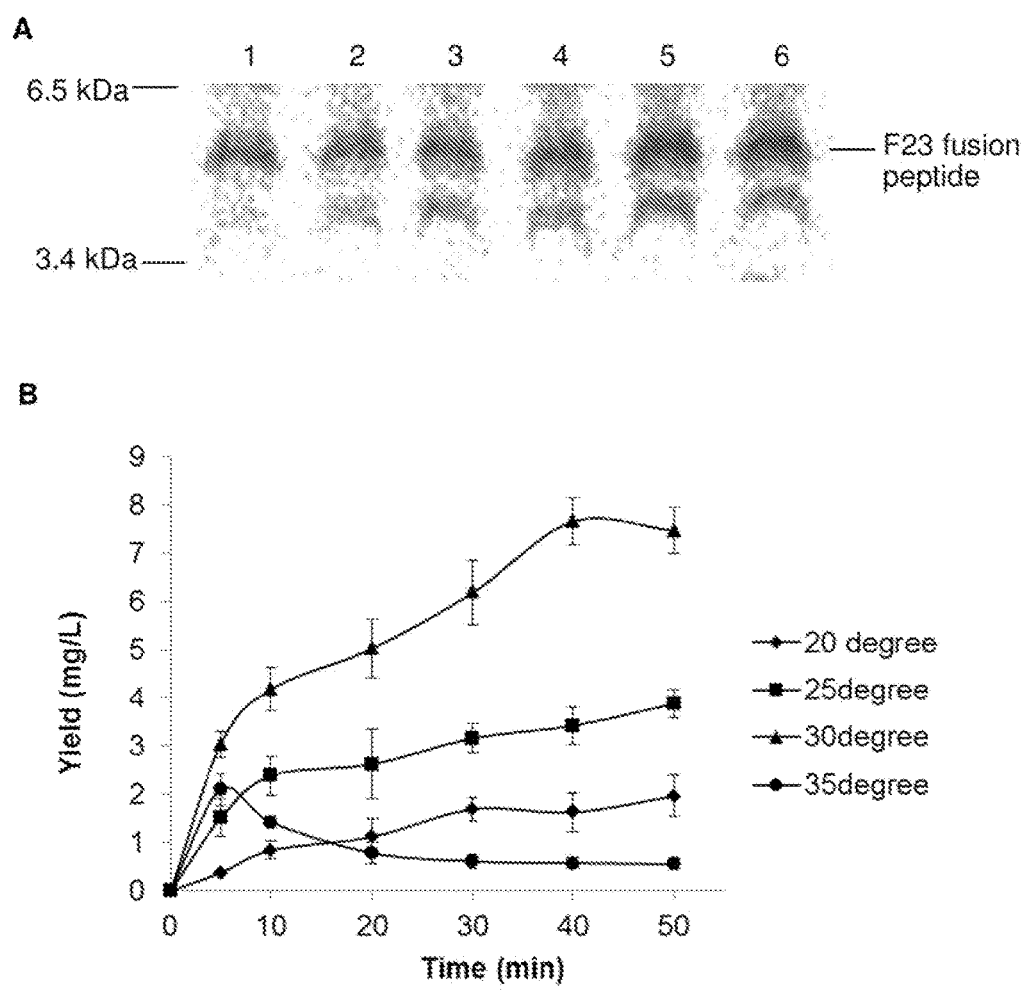
FIG. 2A shows an SDS-PAG analysis of an in vitro synthesis of a F23 fusion protein of the disclosure at 30° C. at different times. The signals were monitored with a phosphorimager. Lane 1, reaction time 5 min.; lane 2, reaction time 10 min.; lane 3, reaction time 20 min.; lane 4, reaction time 30 min.; lane 5, reaction time 40 min.; and lane 6, reaction time 50 min.
FIG. 2B shows the time course of in vitro expression of an F23 fusion protein of the disclosure at different temperatures.

It is well known that short peptides prepared by ribosomal synthesis are quickly digested by cell proteases (Lee K-H, Kwon Y-C, Yoo S J, Kim D-M (2010) Ribosomal synthesis and in situ isolation of peptide molecules in a cell-free translation system. Protein Expr. Purif. 71, 16-20). Therefore, all published approaches for the preparation of active peptides use recombinant technique for translation in vitro, where ribosome-containing S-30 extracts have low less level of proteolytic enzymes than whole cells (Lee K-H, Kwon Y-C, Yoo S J, Kim D-M (2010) Ribosomal synthesis and in situ isolation of peptide molecules in a cell-free translation system. Protein Expr. Purif. 71, 16-20; and Loose C R, Langer R S, Stephanopoulos G N (2007) Optimization of protein fusion partner length for maximizing in vitro translation of peptides. Biotechnol. Prog. 23, 444-451). However, the level of proteolysis is still high especially for short peptides. Optimization of translation condition was performed in in vitro expression system. The F23 peptide (50 amino acids, 5.5 kDa) was expressed in vitro at different temperatures for different lengths of time. As shown in FIG. 2, expression at 30° C. has the highest yield. The expression at 20 and 25° C. has a lower yield because the ribosome has a lower activity to synthesize the peptide. As for the expression at 35° C., the yield of peptide was higher than at 20 and 25° C. during the first 5 min., yet was dramatically decreased after 10 min. This is likely because the proteases in the system have higher activity at 35° C., which decomposes the peptide quickly during the expression period.

In Vivo Expression of Fusion F23 Peptide

Figure 3:
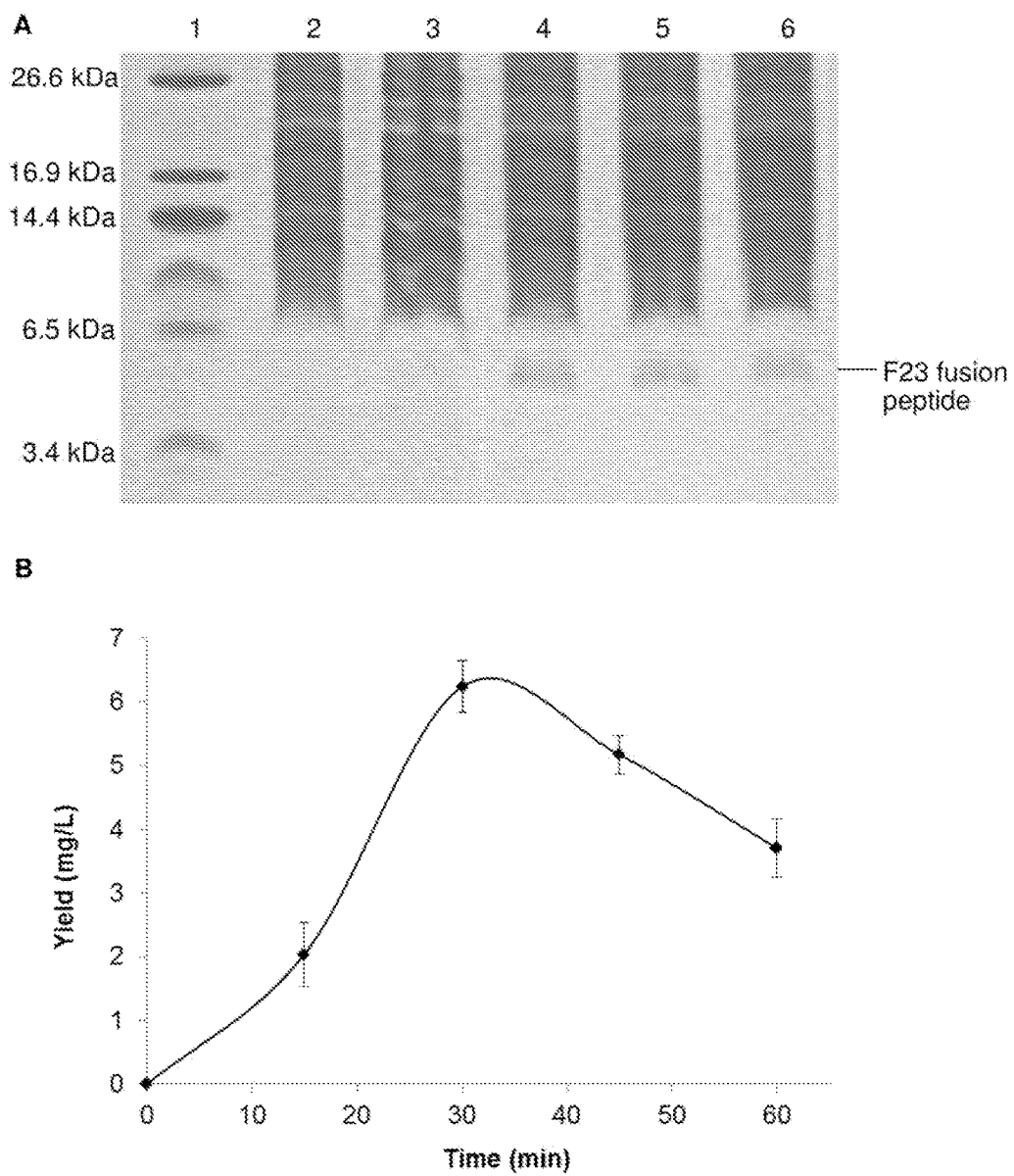
FIG. 3A shows an SDS-PAG analysis of in vivo synthesis of an F23 fusion protein of the disclosure at 30° C. at different times. The gel was stained with Coomassie blue R-250. Lane 1, protein marker; lane 2, expression control without IPTG; lane 3, expression induced with 1 mM IPTG for 15 min.; lane 4, expression induced with 1 mM IPTG for 30 min.; lane 5, expression induced with 1 mM IPTG for 45 min.; lane 6, expression induced with 1 mM IPTG for 60 min.
FIG. 3B shows the time course of in vivo expression of a F23 fusion protein of the disclosure.
Figure 4:
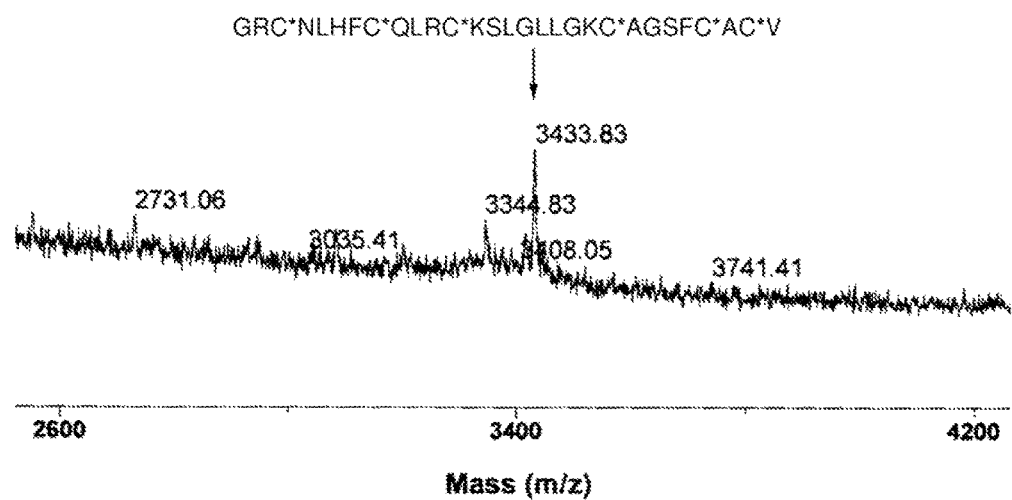
FIG. 4 shows a mass spectrum of F23 after digested by Glu-C. The cysteines were alkylated with 2-iodoacetamide.

The in vitro expression assay showed that temperature is very important for the expression yield of short peptide in the E. coli system. Based on the result of in vitro expression assay, in vivo expression was induced using 1 mM IPTG at 30° C. The time-dependent assay showed that the expression yield was the highest (6 mg/L) at 30 min (FIG. 3). After that, digestion of the fusion peptide was faster than expression. The obtained fusion peptide was confirmed by In-Gel tryptic digest MS and Glu-C digest MS. The molecular weights of trypsin digested peptide fragments are listed in Table 1. The peptide fragment including the whole F23 peptide sequence (m/z 3433, calculate 3430) was obtained by Glu-C digestion (FIG. 4). The yield of fusion F23 peptide in in vivo expression was about 6 mg/L. The cost for preparing the peptide in vivo was much lower than that of in vitro expression and chemical synthesis. The in vivo expression of fusion F23 peptide provides a low-cost and easy-handle method to prepare short peptides.

TABLE 1

MALDI-MS analysis of tryptic digestion of fusion F23 peptide.

| Position peak | Peptide sequence | Calculate peak | m/z |
|---|---|---|---|
| 1-23 | MIHHHHHHEMISLIAALAVIEGR | 2653 | 2653.2 |
| 24-32 | C*NLHFC*QLR | 1247 | 1247.5 |
| 35-41 | SLGLLGK | 687 | 687.4 |
| 42-50 | C*AGSFC*AC*V | 1031 | 1031.3 |

*Cysteines were alkylated with 2-iodoacetamide.

Trapping HIV-1 gp120 Protein for the Detection

Figure 5:
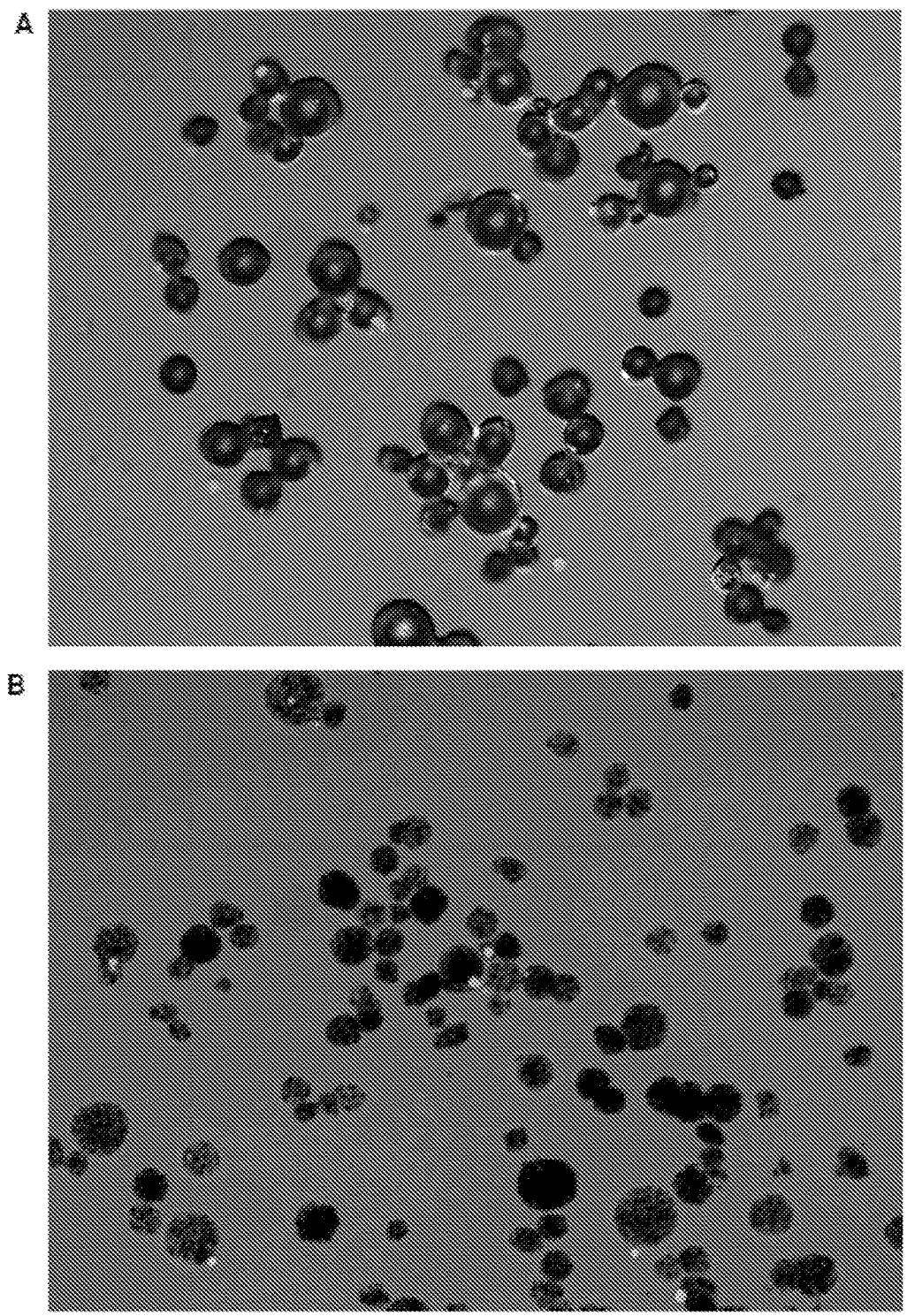
FIG. 5 shows the detection of HIV-1 gp120 protein with FITC-labeled antibody.

The ability of F23 peptide to detect of gp120 protein was evaluated using solid phase methods (FIG. 1B). The fusion F23 peptide sample and the BL21 cell lysate control sample were immobilized on Ni-NTA beads and incubated with an equal amount of pure gp120 protein. Binding of gp120 with beads was evaluated using a gp120 specific monoclonal antibody, labeled with FITC. As shown in FIG. 5, the beads with immobilized F23 peptide can specifically bind with HIV-1 gp120 protein and emit strong green fluorescence after binding to FITC labeled antibody as compared to control beads. It was found that about 1 μg of immobilized F23 can efficiency detect gp120 in 10 ng/μL solution. Very low nonspecific binding was observed using E. coli cell lysate as a control.

Dot Blot Assay to Detect gp120 Protein in Human Serum

Figure 6:
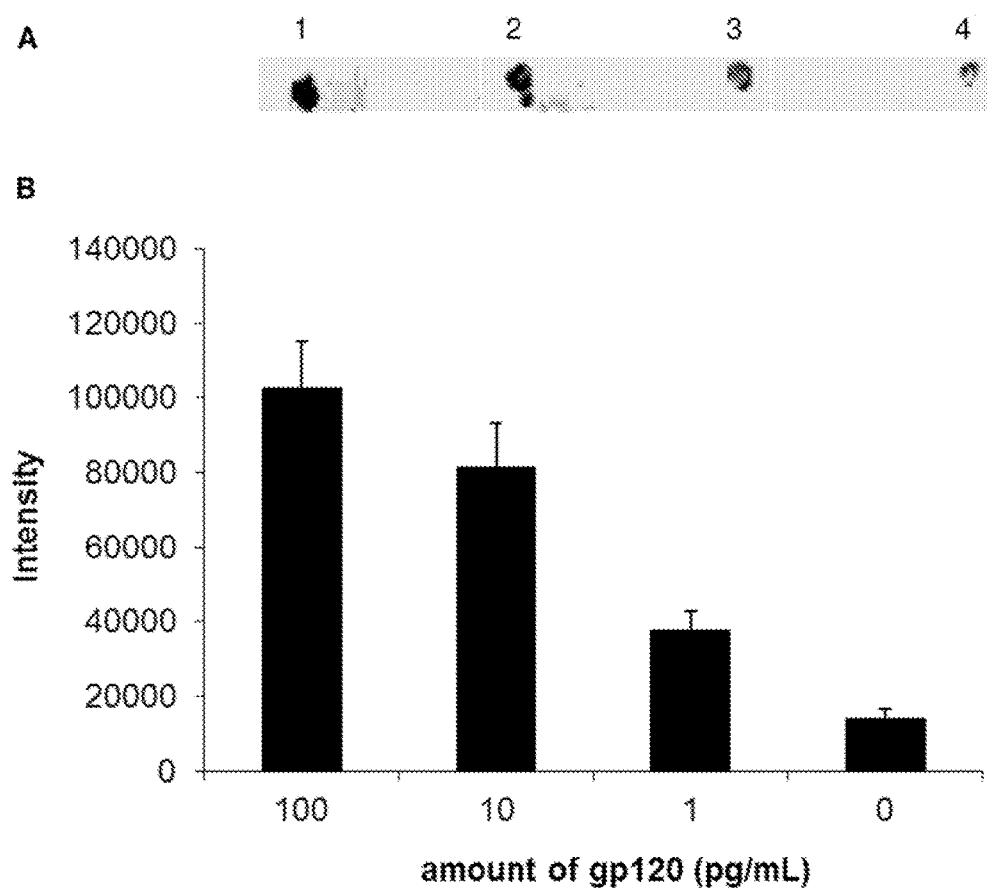
FIG. 6 shows detection of gp120 protein from 10-fold diluted human serum.

Next, the sensitivity of detecting gp120 protein in the presence of human blood was evaluated using a fast and simple dot-immunobinding assay, which used an anti-HIV gp120 antibody conjugated with peroxidase to indicate the gp120 protein. As shown in FIG. 6, this method can detect one picogram gp120 protein from one milliliter 10-fold diluted human serum. Thus, up to 10 pg/mL concentration of gp120 can be detected in human blood, an amount about 20-200 times lower than that of published previously methods that use a pair of monoclonal antibodies (Gilbert M, Kirihara J, Mills J (1991) Enzyme-linked immunoassay for human immunodeficiency virus type 1 envelope glycoprotein 120. J. Clin. Microbiol. 29, 142-147; Rychert J, Strick D, Bazner S, Robinson J, Rosenberg E (2010) Detection of HIV gp120 in plasma during early HIV infection is associated with increased proinflammatory and immunoregulatory cytokines. AIDS Res. Hum. Retroviruses 26, 1139-1145; Santosuosso M, Righi E, Lindstrom V, Leblanc P R, Poznansky M C (2009) HIV-1 envelope protein gp120 is present at high concentration in secondary lymphoid organs of individuals with chronic HIV-1 infection. J. Infect. Dis. 200, 1050-1053; Klasse P J, Moore J P (2004) Is there enough gp120 in the body fluids of HIV-1-infected individuals to have biologically significant effects? Virology 323, 1-8; and Oh S K, Cruikshank W W, Raina J, Blanchard G C, Adler W H, Walker J, Kornfeld H (1992) Identification of HIV-1 envelope glycoprotein in the serum of AIDS and ARC patients. J. Acquir. Immune Defic. Syndr. 5, 251-256).

While particular materials, formulations, operational sequences, process parameters, and end products have been set forth to describe and exemplify this disclosure, they are not intended to be limiting. Rather, it should be noted by those ordinarily skilled in the art that the written disclosures are exemplary only and that various other alternatives, adaptations, and modifications may be made within the scope of the present disclosure. Accordingly, the present disclosure is not limited to the specific embodiments illustrated herein, but is limited only by the following claims.

What is claimed is:

1. A fusion protein comprising a peptide comprising SEQ ID NO:2 or a fragment thereof; and an additional peptide portion.

2. A fusion protein comprising a peptide comprising SEQ ID NO:2 or a fragment thereof and the additional peptide portion comprises SEQ ID NO:3 or a fragment thereof and a polyhistidine sequence.

3. A fusion protein comprising a peptide comprising SEQ ID NO:2 or a fragment thereof and the additional peptide portion comprises SEQ ID NO:4 or a fragment thereof and a polyhistidine sequence.

* * * * *

SEQUENCE LISTING

```
<160> NUMBER OF SEQ ID NOS: 4

<210> SEQ ID NO 1
<211> LENGTH: 27
<212> TYPE: PRT
<213> ORGANISM: Artificial Sequence
<220> FEATURE:
<223> OTHER INFORMATION: F23 peptide

<400> SEQUENCE: 1

Cys Asn Leu His Phe Cys Gln Leu Arg Cys Lys Ser Leu Gly Leu Leu
1               5                   10                  15

Gly Lys Cys Ala Gly Ser Phe Cys Ala Cys Val
            20                  25

<210> SEQ ID NO 2
<211> LENGTH: 121
<212> TYPE: PRT
<213> ORGANISM: Artificial Sequence
<220> FEATURE:
<223> OTHER INFORMATION: F23 peptide

<400> SEQUENCE: 2

Lys Lys Val Val Leu Gly Lys Lys Gly Asp Thr Val Glu Leu Thr Cys
1               5                   10                  15

Thr Ala Ser Gly Lys Lys Ser Ile Gly Phe His Trp Lys Asn Ser Asn
            20                  25                  30

Gly Ile Lys Ile Leu Gly Asn Gly Ser Phe Leu Thr Lys Gly Pro
        35                  40                  45

Ser Lys Leu Asn Asp Arg Ala Asp Ser Arg Arg Ser Leu Trp Asp Gly
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gly Lys Glu Val Gly Leu Leu
                85                  90                  95

Val Phe Gly Leu Thr Arg Ala Asn Ser Asp Thr His Leu Leu Gly Gly
            100                 105                 110

Gly Ser Leu Thr Leu Thr Leu Glu Ser
        115                 120
```

```
<210> SEQ ID NO 3
<211> LENGTH: 15
<212> TYPE: PRT
<213> ORGANISM: Artificial Sequence
<220> FEATURE:
<223> OTHER INFORMATION: Additional peptide portion

<400> SEQUENCE: 3

Glu Met Ile Ser Leu Ile Ala Ala Leu Ala Val Ile Glu Gly Arg
1               5                   10                  15

<210> SEQ ID NO 4
<211> LENGTH: 51
<212> TYPE: PRT
<213> ORGANISM: Artificial Sequence
<220> FEATURE:
<223> OTHER INFORMATION: Additional peptide portion

<400> SEQUENCE: 4

Glu Met Ile Ser Leu Ile Ala Ala Leu Ala Val Asp Arg Val Ile Gly
1               5                   10                  15

Met Glu Asn Ala Met Pro Trp Asn Leu Pro Ala Asp Leu Ala Trp Phe
            20                  25                  30

Lys Arg Asn Thr Leu Asn Lys Pro Val Ile Met Gly Arg His Thr Trp
        35                  40                  45

Glu Ser Ile
    50
```